(12) United States Patent
Papas (10) Patent No.: US 10,688,107 B2
(45) Date of Patent: Jun. 23, 2020

(54) SCALABLE VITAMIN COMPOSITION UNIT DOSAGE FOR THE TREATMENT OF FAT-SOLUBLE VITAMIN DEFICIENCIES

(71) Applicant: Callion Pharma, LLC, Jonesborough, TN (US)

(72) Inventor: Konstantinos Andreas Papas, Jonesborough, TN (US)

(73) Assignee: Callion Pharma, LLC, Jonesborough, TN (US)

( * ) Notice: Subject to any disclaimer, the term of this patent is extended or adjusted under 35 U.S.C. 154(b) by 18 days.

(21) Appl. No.: 15/558,622

(22) PCT Filed: Mar. 18, 2016

(86) PCT No.: PCT/US2016/023229
§ 371 (c)(1),
(2) Date: Sep. 15, 2017

(87) PCT Pub. No.: WO2016/149655
PCT Pub. Date: Sep. 22, 2016

(65) Prior Publication Data
US 2018/0177804 A1    Jun. 28, 2018

Related U.S. Application Data

(60) Provisional application No. 62/134,818, filed on Mar. 18, 2015.

(51) Int. Cl.
| | |
|---|---|
| *A61K 31/593* | (2006.01) |
| *A61K 31/122* | (2006.01) |
| *A61K 31/015* | (2006.01) |
| *A61K 31/23* | (2006.01) |
| *A61K 31/355* | (2006.01) |
| *A61K 31/592* | (2006.01) |
| *A61K 31/07* | (2006.01) |
| *A61K 31/203* | (2006.01) |
| *A61K 9/08* | (2006.01) |
| *A61K 9/48* | (2006.01) |

(52) U.S. Cl.
CPC .............. *A61K 31/593* (2013.01); *A61K 9/08* (2013.01); *A61K 9/48* (2013.01); *A61K 31/015* (2013.01); *A61K 31/07* (2013.01); *A61K 31/122* (2013.01); *A61K 31/203* (2013.01); *A61K 31/23* (2013.01); *A61K 31/355* (2013.01); *A61K 31/592* (2013.01)

(58) Field of Classification Search
CPC .......... A61K 31/593; A61K 9/48; A61K 9/08; A61K 31/592; A61K 31/355; A61K 31/23; A61K 31/203; A61K 31/015; A61K 31/122; A61K 31/07
See application file for complete search history.

(56) References Cited

U.S. PATENT DOCUMENTS

| | | | |
|---|---|---|---|
| 2005/0209315 A1 | 9/2005 | Papas et al. | |
| 2008/0070845 A1* | 3/2008 | Thompson | ........... A61K 31/335 514/26 |
| 2013/0059795 A1 | 3/2013 | Lo et al. | |
| 2014/0017337 A1 | 1/2014 | Amoruso | |

FOREIGN PATENT DOCUMENTS

| | | |
|---|---|---|
| WO | 2005063218 | 7/2005 |
| WO | 2008070308 | 6/2008 |

OTHER PUBLICATIONS

Argao et al, Pediatric Research, vol. 31, No. 2, 146-150 (Year: 1992).*
EFSA document, The EFSA Journal, 490, 1-20 (Year: 2007).*
Haskell et al, "Recovery from impaired dark adaptation in nightblind pregnant Nepali woman who receives small daily doses of vitamin A as amarinth leaves, carrots, goat liver, vitamin A-fortified rice, or retinyl palmitate," American Journal of Clinical Nutrition, vol. 81, 2005, pp. 461-471.
Omenn, et al, "Effects of a Combination of Beta Carotene and Vitamin A on Lung Cancer and Cardiovascular Disease," The New England Journal of Medicine, vol. 334, May 2, 1996, pp. 1150-1155.
International Search Report and Written Opinion for corresponding PCT/US2016/023229 dated Jun. 10, 2016.
Search Report for European Patent Application No. 16765854.1 dated Jun. 22, 2018.
Adams, "d-Alpha Tocopheryl Polyethylene Glycol 1000 Succinate (Eastman Vitamin E. TPGS) as an Emulsifier and Bioenhancer for Drugs and Lipophilic Compounds", International Congress of Technology and Pharmacology, Assoc. Pharm. Galenique Ind., Chatenay Malabry, FR, vol. 4, No. 4, pp. 254-262, Jan. 1, 1992.
Anonymous, "Product Information, name of Medicine: Vitalipid N. Infant and Adult, Multivitamin oily injection", Internet Citation, http://222.medsafe.govt.nz/profs/datas/heet/v/VitalipidNinj.pdf, pp. 1-4, Mar. 3, 2010.
Feranchak et al., "Prospective, long-term study of fat-soluble vitamin status in children with cystic fibrosis identified by newborn screen", Journal of Pediatrics, Mosby-Year Book, St. Louis, MO, vol. 135, No. 5, Nov. 1, 1999.
Veter, "Vitamine and Spurenelemente in der parenteralen Ernahrung", Pharmazie in Unser Zeit, vol. 38, No. 2, pp. 148-153, Mar. 1, 2009.
Willig et al., "Diatetic in der Langzeitbehandlung pankreasoperierter Patienten/Dietetic care of patents after pancreatic surgery", Verdauunskrankheiten, Dustri-Verlag Feistle, Muenchen, DE, vol. 10, No. 1, pp. 19-25, Jan. 1, 1992.

* cited by examiner

*Primary Examiner* — Sudhakar Katakam
(74) *Attorney, Agent, or Firm* — Dinsmore & Shohl LLP (57) ABSTRACT

A scalable vitamin composition unit dosage adapted to treat a fat-soluble vitamin deficiency in a subject is provided herein, the unit dosage consisting essentially of vitamin D, vitamin E, vitamin K, and vitamin A, wherein the unit dosage is substantially free of additional vitamins and wherein the unit dosage is scalable based on the weight, age, and condition of a subject without inducing toxic effects. Also provided are methods of treating a fat-soluble vitamin deficiency in a subject in need thereof by administering to the subject an effective amount of a unit dosage as described herein.

14 Claims, 6 Drawing Sheets

Fig. 1

Dietary Reference Intakes (DRIs): Tolerable Upper Intake Levels, Vitamins
Food and Nutrition Board, Institute of Medicine, National Academies

| Life Stage Group | Vitamin A (µg/d)[a] | Vitamin C (mg/d) | Vitamin D (µg/d) | Vitamin E (mg/d)[b,c] | Vitamin K | Thiamin | Riboflavin | Niacin (mg/d)[c] | Vitamin B$_6$ (mg/d) | Folate (µg/d)[c] | Vitamin B$_{12}$ | Pantothenic Acid | Biotin | Choline (g/d) | Carotenoids[d] |
|---|---|---|---|---|---|---|---|---|---|---|---|---|---|---|---|
| Infants | | | | | | | | | | | | | | | |
| 0 to 6 mo | 600 | ND[e] | 25 | ND | ND | ND | ND | ND | ND | ND | ND | ND | ND | ND | ND |
| 6 to 12 mo | 600 | ND | 38 | ND | ND | ND | ND | ND | ND | ND | ND | ND | ND | ND | ND |
| Children | | | | | | | | | | | | | | | |
| 1-3 y | 600 | 400 | 63 | 200 | ND | ND | ND | 10 | 30 | 300 | ND | ND | ND | 1.0 | ND |
| 4-8 y | 900 | 650 | 75 | 300 | ND | ND | ND | 15 | 40 | 400 | ND | ND | ND | 1.0 | ND |
| Males | | | | | | | | | | | | | | | |
| 9-13 y | 1,700 | 1,200 | 100 | 600 | ND | ND | ND | 20 | 60 | 600 | ND | ND | ND | 2.0 | ND |
| 14-18 y | 2,800 | 1,800 | 100 | 800 | ND | ND | ND | 30 | 80 | 800 | ND | ND | ND | 3.0 | ND |
| 19-30 y | 3,000 | 2,000 | 100 | 1,000 | ND | ND | ND | 35 | 100 | 1,000 | ND | ND | ND | 3.5 | ND |
| 31-50 y | 3,000 | 2,000 | 100 | 1,000 | ND | ND | ND | 35 | 100 | 1,000 | ND | ND | ND | 3.5 | ND |
| 51-70 y | 3,000 | 2,000 | 100 | 1,000 | ND | ND | ND | 35 | 100 | 1,000 | ND | ND | ND | 3.5 | ND |
| > 70 y | 3,000 | 2,000 | 100 | 1,000 | ND | ND | ND | 35 | 100 | 1,000 | ND | ND | ND | 3.5 | ND |
| Females | | | | | | | | | | | | | | | |
| 9-13 y | 1,700 | 1,200 | 100 | 600 | ND | ND | ND | 20 | 60 | 600 | ND | ND | ND | 2.0 | ND |
| 14-18 y | 2,800 | 1,800 | 100 | 800 | ND | ND | ND | 30 | 80 | 800 | ND | ND | ND | 3.0 | ND |
| 19-30 y | 3,000 | 2,000 | 100 | 1,000 | ND | ND | ND | 35 | 100 | 1,000 | ND | ND | ND | 3.5 | ND |
| 31-50 y | 3,000 | 2,000 | 100 | 1,000 | ND | ND | ND | 35 | 100 | 1,000 | ND | ND | ND | 3.5 | ND |
| 51-70 y | 3,000 | 2,000 | 100 | 1,000 | ND | ND | ND | 35 | 100 | 1,000 | ND | ND | ND | 3.5 | ND |
| > 70 y | 3,000 | 2,000 | 100 | 1,000 | ND | ND | ND | 35 | 100 | 1,000 | ND | ND | ND | 3.5 | ND |
| Pregnancy | | | | | | | | | | | | | | | |
| 14-18 y | 2,800 | 1,800 | 100 | 800 | ND | ND | ND | 30 | 80 | 800 | ND | ND | ND | 3.0 | ND |
| 19-30 y | 3,000 | 2,000 | 100 | 1,000 | ND | ND | ND | 35 | 100 | 1,000 | ND | ND | ND | 3.5 | ND |
| 31-50 y | 3,000 | 2,000 | 100 | 1,000 | ND | ND | ND | 35 | 100 | 1,000 | ND | ND | ND | 3.5 | ND |
| Lactation | | | | | | | | | | | | | | | |
| 14-18 y | 2,800 | 1,800 | 100 | 800 | ND | ND | ND | 30 | 80 | 800 | ND | ND | ND | 3.0 | ND |
| 19-30 y | 3,000 | 2,000 | 100 | 1,000 | ND | ND | ND | 35 | 100 | 1,000 | ND | ND | ND | 3.5 | ND |
| 31-50 y | 3,000 | 2,000 | 100 | 1,000 | ND | ND | ND | 35 | 100 | 1,000 | ND | ND | ND | 3.5 | ND |

NOTE: A Tolerable Upper Intake Level (UL) is the highest level of daily nutrient intake that is likely to pose no risk of adverse health effects to almost all individuals in the general population. Unless otherwise specified, the UL represents total intake from food, water and supplements. Due to a lack of suitable data, ULs could not be established for vitamin K, thiamin, riboflavin, vitamin B$_{12}$, pantothenic acid, biotin, and carotenoids. In the absence of a UL, extra caution may be warranted in consuming levels above recommended intakes. Members of the general population should be advised not to routinely exceed the UL. The UL is not meant to apply to individuals who are treated with the nutrient under medical supervision or to individuals with predisposing conditions that modify their sensitivity to the nutrient.

[a] As preformed vitamin A only.
[b] As α-tocopherol; applies to any form of supplemental α-tocopherol.
[c] The ULs for vitamin E, niacin, and folate apply to synthetic form supplements, fortified foods, or a combination of the two.
[d] β-Carotene supplements are advised only to serve as a provitamin A source for individuals at risk of vitamin A deficiency
[e] ND=Not determinable due to lack of data of adverse effects in this age group and concern with regard to lack of ability to handle excess amounts. Source of intake should be from food only to prevent high levels of intake.

Fig. 2

Dietary Reference Intakes (DRIs): Tolerable Upper Intake Levels, Elements
Food and Nutrition Board, Institute of Medicine, National Academies

| Life Stage Group | Arsenic[a] | Boron (mg/d) | Calcium (mg/d) | Chromium | Copper (μg/d) | Fluoride (mg/d) | Iodine (μg/d) | Iron (mg/d) | Magnesium (mg/d)[b] | Manganese (mg/d) | Molybdenum (μg/d) | Nickel (mg/d) | Phosphorus (g/d) | Selenium (μg/d) | Silicon[c] | Vanadium (mg/d)[d] | Zinc (mg/d) | Sodium (g/d) | Chloride (g/d) |
|---|---|---|---|---|---|---|---|---|---|---|---|---|---|---|---|---|---|---|---|
| Infants | | | | | | | | | | | | | | | | | | | |
| 0 to 6 mo | ND[e] | ND | 1,000 | ND | ND | 0.7 | ND | 40 | ND | ND | ND | ND | ND | 45 | ND | ND | 4 | ND | ND |
| 6 to 12 mo | ND | ND | 1,500 | ND | ND | 0.9 | ND | 40 | ND | ND | ND | ND | ND | 60 | ND | ND | 5 | ND | ND |
| Children | | | | | | | | | | | | | | | | | | | |
| 1-3 y | ND | 3 | 2,500 | ND | 1,000 | 1.3 | 200 | 40 | 65 | 2 | 300 | 0.2 | 3 | 90 | ND | ND | 7 | 1.5 | 2.3 |
| 4-8 y | ND | 6 | 2,500 | ND | 3,000 | 2.2 | 300 | 40 | 110 | 3 | 600 | 0.3 | 3 | 150 | ND | ND | 12 | 1.9 | 2.9 |
| Males | | | | | | | | | | | | | | | | | | | |
| 9-13 y | ND | 11 | 3,000 | ND | 5,000 | 10 | 600 | 40 | 350 | 6 | 1,100 | 0.6 | 4 | 280 | ND | ND | 23 | 2.2 | 3.4 |
| 14-18 y | ND | 17 | 3,000 | ND | 8,000 | 10 | 900 | 45 | 350 | 9 | 1,700 | 1.0 | 4 | 400 | ND | ND | 34 | 2.3 | 3.6 |
| 19-30 y | ND | 20 | 2,500 | ND | 10,000 | 10 | 1,100 | 45 | 350 | 11 | 2,000 | 1.0 | 4 | 400 | ND | 1.8 | 40 | 2.3 | 3.6 |
| 31-50 y | ND | 20 | 2,500 | ND | 10,000 | 10 | 1,100 | 45 | 350 | 11 | 2,000 | 1.0 | 4 | 400 | ND | 1.8 | 40 | 2.3 | 3.6 |
| 51-70 y | ND | 20 | 2,000 | ND | 10,000 | 10 | 1,100 | 45 | 350 | 11 | 2,000 | 1.0 | 4 | 400 | ND | 1.8 | 40 | 2.3 | 3.6 |
| >70 y | ND | 20 | 2,000 | ND | 10,000 | 10 | 1,100 | 45 | 350 | 11 | 2,000 | 1.0 | 3 | 400 | ND | 1.8 | 40 | 2.3 | 3.6 |
| Females | | | | | | | | | | | | | | | | | | | |
| 9-13 y | ND | 11 | 3,000 | ND | 5,000 | 10 | 600 | 40 | 350 | 6 | 1,100 | 0.6 | 4 | 280 | ND | ND | 23 | 2.2 | 3.4 |
| 14-18 y | ND | 17 | 3,000 | ND | 8,000 | 10 | 900 | 45 | 350 | 9 | 1,700 | 1.0 | 4 | 400 | ND | ND | 34 | 2.3 | 3.6 |
| 19-30 y | ND | 20 | 2,500 | ND | 10,000 | 10 | 1,100 | 45 | 350 | 11 | 2,000 | 1.0 | 4 | 400 | ND | 1.8 | 40 | 2.3 | 3.6 |
| 31-50 y | ND | 20 | 2,500 | ND | 10,000 | 10 | 1,100 | 45 | 350 | 11 | 2,000 | 1.0 | 4 | 400 | ND | 1.8 | 40 | 2.3 | 3.6 |
| 51-70 y | ND | 20 | 2,000 | ND | 10,000 | 10 | 1,100 | 45 | 350 | 11 | 2,000 | 1.0 | 4 | 400 | ND | 1.8 | 40 | 2.3 | 3.6 |
| >70 y | ND | 20 | 2,000 | ND | 10,000 | 10 | 1,100 | 45 | 350 | 11 | 2,000 | 1.0 | 3 | 400 | ND | 1.8 | 40 | 2.3 | 3.6 |
| Pregnancy | | | | | | | | | | | | | | | | | | | |
| 14-18 y | ND | 17 | 3,000 | ND | 8,000 | 10 | 900 | 45 | 350 | 9 | 1,700 | 1.0 | 3.5 | 400 | ND | ND | 34 | 2.3 | 3.6 |
| 19-30 y | ND | 20 | 2,500 | ND | 10,000 | 10 | 1,100 | 45 | 350 | 11 | 2,000 | 1.0 | 3.5 | 400 | ND | ND | 40 | 2.3 | 3.6 |
| 31-50 y | ND | 20 | 2,500 | ND | 10,000 | 10 | 1,100 | 45 | 350 | 11 | 2,000 | 1.0 | 3.5 | 400 | ND | ND | 40 | 2.3 | 3.6 |
| Lactation | | | | | | | | | | | | | | | | | | | |
| 14-18 y | ND | 17 | 3,000 | ND | 8,000 | 10 | 900 | 45 | 350 | 9 | 1,700 | 1.0 | 4 | 400 | ND | ND | 34 | 2.3 | 3.6 |
| 19-30 y | ND | 20 | 2,500 | ND | 10,000 | 10 | 1,100 | 45 | 350 | 11 | 2,000 | 1.0 | 4 | 400 | ND | ND | 40 | 2.3 | 3.6 |
| 31-50 y | ND | 20 | 2,500 | ND | 10,000 | 10 | 1,100 | 45 | 350 | 11 | 2,000 | 1.0 | 4 | 400 | ND | ND | 40 | 2.3 | 3.6 |

NOTE: A Tolerable Upper Intake Level (UL) is the highest level of daily nutrient intake that is likely to pose no risk of adverse health effects to almost all individuals in the general population. Unless otherwise specified, the UL represents total intake from food, water and supplements. Due to a lack of suitable data, ULs could not be established for vitamin K, thiamin, riboflavin, vitamin B$_{12}$, pantothenic acid, biotin, and carotenoids. In the absence of a UL, extra caution may be warranted in consuming levels above recommended intakes. Members of the general population should be advised not to routinely exceed the UL. The UL is not meant to apply to individuals who are treated with the nutrient under medical supervision or to individuals with predisposing conditions that modify their sensitivity to the nutrient.

[a] Although the UL was not determined for arsenic, there is no justification for adding arsenic to food or supplements.
[b] The ULs for magnesium represent intake from a pharmacological agent only and do not include intake from food and water.
[c] Although silicon has not been shown to cause adverse effects in humans, there is no justification for adding silicon to supplements.
[d] Although vanadium in food has not been shown to cause adverse effects in humans, there is no justification for adding vanadium to food and vanadium supplements should be used with caution. The UL is based on adverse effects in laboratory animals and this data could be used to set a UL for adults but not children and adolescents.
[e] ND=Not determinable due to lack of data of adverse effects in this age group and concern with regard to lack of ability to handle excess amounts. Source of intake should be from food only to prevent high levels of intake.

Fig. 3

Table 1 – Scaled Unit Dosage of Exemplary Vitamin Composition

| Scaling factor | Liquid (ml) | Vitamin A (IU) | Vitamin D (IU) | Vitamin E (IU) | Vitamin K (mcg) |
|---|---|---|---|---|---|
| 1 | 0.5 | 1000 | 1000 | 37.5 | 1000 |
| 2 | 1.0 | 2000 | 2000 | 75 | 2000 |
| 3 | 1.5 | 3000 | 3000 | 112.5 | 3000 |
| 4 | 2.0 | 4000 | 4000 | 150 | 4000 |
| 5 | 2.5 | 5000 | 5000 | 187.5 | 5000 |
| 6 | 3.0 | 6000 | 6000 | 225 | 6000 |
| 7 | 3.5 | 7000 | 7000 | 262.5 | 7000 |
| 8 | 4.0 | 8000 | 8000 | 300 | 8000 |
| 9 | 4.5 | 9000 | 9000 | 337.5 | 9000 |
| 10 | 5.0 | 10,000 | 10,000 | 375 | 10,000 |

Fig. 4

Table 2 – Scaled Unit Dosage of AquADEKs® Liquid Formulation

| Scaling factor | Liquid (ml) | Vitamin A (IU) | Vitamin D (IU) | Vitamin E (IU) | Vitamin K (mcg) | Zinc (mg) |
|---|---|---|---|---|---|---|
| 1 | 1 | 5751 | 600 | 50 | 400 | 5 |
| 2 | 2 | 11502 | 1200 | 100 | 800 | 10 |
| 3 | 3 | 17253 | 1800 | 150 | 1200 | 15 |
| 4 | 4 | 23004 | 2400 | 200 | 1600 | 20 |
| 5 | 5 | 28755 | 3000 | 250 | 2000 | 25 |
| 6 | 6 | 34506 | 3600 | 300 | 2400 | 30 |
| 7 | 7 | 40257 | 4200 | 350 | 2800 | 35 |
| 8 | 8 | 46008 | 4800 | 400 | 3200 | 40 |
| 9 | 9 | 51759 | 5400 | 450 | 3600 | 45 |
| 10 | 10 | 57510 | 6000 | 500 | 4000 | 50 |
| 11 | 11 | 63261 | 6600 | 550 | 4400 | 55 |

Fig. 5

Table 3 – Scaled Unit Dosage of Flintstones™ Complete

| Scaling factor | Tablet Number | Vitamin A (IU) | Vitamin D (IU) | Vitamin E (IU) | Vitamin K (mcg) | Zinc (mg) | Iron (mg) | Copper (mg) | Niacin (mg) |
|---|---|---|---|---|---|---|---|---|---|
| 1 | 1 | 3000 | 600 | 30 | 55 | 12 | 18 | 2 | 15 |
| 2 | 2 | 6000 | 1200 | 60 | 110 | 24 | 36 | 4 | 30 |
| 3 | 3 | 9000 | 1800 | 90 | 165 | 36 | 54 | 6 | 45 |
| 4 | 4 | 12000 | 2400 | 120 | 220 | 48 | 72 | 8 | 60 |
| 5 | 5 | 15000 | 3000 | 150 | 275 | 60 | 90 | 10 | 75 |
| 6 | 6 | 18000 | 3600 | 180 | 660 | 72 | 108 | 12 | 90 |
| 7 | 7 | 21000 | 4200 | 210 | 385 | 84 | 126 | 14 | 105 |
| 8 | 8 | 24000 | 4800 | 240 | 440 | 96 | 144 | 16 | 120 |
| 9 | 9 | 27000 | 5400 | 270 | 495 | 108 | 162 | 18 | 135 |
| 10 | 10 | 30000 | 6000 | 300 | 550 | 120 | 180 | 20 | 150 |
| 11 | 11 | 33000 | 6600 | 330 | 605 | 132 | 198 | 22 | 165 |

Fig. 6

Table 4 - Scaled Unit Dosage of Poly-Vi-Sol® without Iron

| Scaling factor | Liquid (ml) | Vitamin A (IU) | Vitamin D (IU) | Vitamin E (IU) | Vitamin K (mcg) | Niacin (mg) |
|---|---|---|---|---|---|---|
| 1 | 1 | 1500 | 400 | 5 | -- | 8 |
| 2 | 2 | 3000 | 800 | 10 | -- | 16 |
| 3 | 3 | 4500 | 1200 | 15 | -- | 24 |
| 4 | 4 | 6000 | 1600 | 20 | -- | 32 |
| 5 | 5 | 7500 | 2000 | 25 | -- | 40 |
| 6 | 6 | 9000 | 2400 | 30 | -- | 48 |
| 7 | 7 | 10500 | 2800 | 35 | -- | 56 |
| 8 | 8 | 12000 | 3200 | 40 | -- | 64 |
| 9 | 9 | 13500 | 3600 | 45 | -- | 72 |
| 10 | 10 | 15000 | 4000 | 50 | -- | 80 |
| 11 | 11 | 16500 | 4400 | 55 | -- | 88 |

SCALABLE VITAMIN COMPOSITION UNIT DOSAGE FOR THE TREATMENT OF FAT-SOLUBLE VITAMIN DEFICIENCIES

CROSS-REFERENCE TO RELATED APPLICATION

The present application claims priority to U.S. Provisional Application 62/134,818 filed Mar. 18, 2015, the entirety of which is incorporated herein by this reference.

TECHNICAL FIELD

The presently disclosed subject matter relates to scalable vitamin composition unit dosages adapted to treat a fat-soluble vitamin deficiency in a subject.

BACKGROUND ART

Certain diseases, conditions, surgeries, procedures, and medications are associated with malabsorption of fat, which can lead to serious deficiencies of the fat-soluble vitamins D, E, K, and A. For example, individuals suffering from cholestatic liver disease, cystic fibrosis, Crohn's Disease, post-bariatric procedures, and many other conditions may experience severe deficiencies of vitamins D, E, K, and A.

Supplementation with standard multi-vitamins often fails to correct serious deficiencies associated with malabsorption of fat. First, standard multi-vitamins often fail to provide doses of vitamins D, E, K, and A of sufficient strength to correct deficiencies resulting from malabsorption of fat. Second, standard multivitamins generally contain additional vitamins other than vitamins D, E, K, and A (such as selenium, zinc, copper, and iron), such that increasing the dose of the multivitamin to deliver enough of vitamins D, E, K, and A results in toxicity of one or more other vitamins or minerals contained in the multivitamin formula. Third, fat-soluble vitamin deficiency cannot be corrected in certain conditions only by increasing the dosage and requires the use of technology to facilitate absorption.

The need exists to develop a scalable vitamin formulation comprising vitamins D, E, K, and A, wherein the composition unit dosage is scalable based on weight, age, and condition of a subject, without inducing adverse toxic effects.

SUMMARY

Provided herein is a scalable vitamin composition unit dosage adapted to treat a fat-soluble vitamin deficiency in a subject, the vitamin composition consisting essentially of: vitamin D in a form selected from the group consisting of cholecalciferol, ergocalciferol, and combinations thereof; vitamin E in the form of d-alpha tocopherol polyethylene glycol 1000 succinate (TPGS) or a combination of TPGS and another form of vitamin E; vitamin K in a form selected from the group consisting of phytonadione, menaquinone, and combinations thereof; and vitamin A in a form selected from the group consisting of retinol, retinyl esters, retinal, retinoic acid, carotenoids, and combinations thereof; wherein the unit dosage is substantially free of additional vitamins and wherein the unit dosage of the vitamin composition is scalable based on weight, age, and condition of a subject, without inducing adverse toxic effects.

In another embodiment, a scalable vitamin composition unit dosage adapted to treat a fat-soluble vitamin deficiency in a subject is provided, the unit dosage consisting essentially of: from about 500 to about 4000 IU vitamin D in the form of cholecalciferol; from about 18 to about 300 IU vitamin E in the form of d-alpha tocopheryl polyethylene glycol 1000 succinate (TPGS) or a combination of TPGS and another form of vitamin E; from about 500 to about 4000 mcg vitamin K in the form of phytonadione; and from about 500 to about 4000 IU vitamin A in a form selected from the group consisting of retinyl palmitate, beta-carotene, and combinations thereof, wherein the unit dosage is substantially free of additional vitamins and wherein the unit dosage of the vitamin composition is scalable based on weight, age, and condition of the subject, without inducing adverse toxic effects.

In another embodiment, a method of treating a fat-soluble vitamin deficiency in a subject in need thereof is provided, the method comprising: (a) providing a scalable vitamin composition unit dosage consisting essentially of: from about 500 to about 4000 IU vitamin D in a form of cholecalciferol; from about 18 to about 300 IU vitamin E in a form of alpha-tocopherol from TPGS or a combination of TPGS and another form of vitamin E; from about 500 to about 4000 mcg vitamin K in a form of phytonadione; and from about 500 to about 4000 IU vitamin A in a form of a combination of retinol from retinyl palmitate and beta-carotene; (b) determining the levels of vitamins D, E, K, and A needed to treat the fat-soluble vitamin deficiency; (c) scaling up the unit dosage provided in step (a) by multiplying the unit dosage by a scaling factor in order to provide the levels determined in step (b); and (d) administering the scaled dosage of step (c), wherein the fat-soluble vitamin deficiency is treated in the subject without inducing toxic effects.

These and other objects, features, embodiments, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified.

BRIEF DESCRIPTION OF DRAWINGS

FIG. 1 shows the Tolerable Upper Intake Levels (ULs) of vitamin A, vitamin C, vitamin D, vitamin E, vitamin K, thiamin, riboflavin, niacin, vitamin $B_6$, folate, vitamin $B_{12}$, pantothenic acid, biotin, choline, and carotenoids, as set by the Institute of Medicine. The data is culled from reports available at www.nap.edu, including: *Dietary Reference Intakes for Calcium, Phosphorous, Magnesium, Vitamin D, and Fluoride* (1997); *Dietary Reference Intakes for Thiamin, Riboflavin, Niacin, Vitamin $B_6$, Folate, Vitamin $B_{12}$, Pantothenic Acid, Biotin, and Choline* (1998); *Dietary Reference Intakes for Vitamin C, Vitamin E, Selenium, and Carotenoids* (2000); *Dietary Reference Intakes for Vitamin A, Vitamin K, Arsenic, Boron, Chromium, Copper, Iodine, Iron, Manganese, Molybdenum, Nickel, Silicon, Vanadium, and Zinc* (2001); and *Dietary Reference Intakes for Calcium and Vitamin D* (2011). The FIG. 1 guidelines are published by the Institute of Medicine at www.iom.edu.

FIG. 2 shows the Tolerable Upper Intake Levels (ULs) of arsenic, boron, calcium, chromium, copper, fluoride, iodine, iron, magnesium, manganese, molybdenum, nickel, phosphorous, selenium, silicon, vanadium, zinc, sodium, and chloride, as set by the Institutes of Medicine. As noted for FIG. 1, the FIG. 2 guidelines are published by the Institute of Medicine and may be accessed at www.iom.edu.

DESCRIPTION OF EMBODIMENTS

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by those of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±25%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The terms "treat," "treatment," and "treating," as used herein, refer to a method of alleviating or abrogating a disease, disorder, deficiency, and/or symptoms thereof.

The Institute of Medicine (IOM) tolerable upper intake level (UL) is the highest average daily intake level of a vitamin that is likely to pose no risk of adverse health effects to almost all individuals in the general population. As intake increases above the UL, the potential risk of adverse effects may increase. FIGS. 1-2 set forth the IOM published guidelines for vitamin ULs, based on age, sex, and conditions including pregnancy and lactation.

Vitamin D is a fat-soluble secosteroid that enhances intestinal absorption of calcium. Vitamin D has other roles in the body, including modulation of cell growth, neuromuscular and immune function, and reduction of inflammation. Vitamin D comprises various forms, including the two primary forms in humans, cholecalciferol (vitamin $D_3$) and ergocalciferol (vitamin $D_2$). Vitamin $D_3$ is produced photochemically in the skin upon exposure to sunlight. Vitamin D is also ingested from diet or supplements. Deficiency of vitamin D results in impaired bone mineralization and bone softening diseases, including rickets and osteomalacia. The UL for vitamin D in healthy adults is 4,000 IU/day (100 mcg/day). Hypervitaminosis D may cause hypercalcemia, abdominal pain, nausea/vomiting, dehydration, anorexia, and constipation.

Vitamin E refers to a group of eight fat-soluble compounds that include four tocopherols and four tocotrienols. Each is identified by a prefix alpha (α), beta (β), gamma (γ), and delta (δ). Alpha-tocopherol is an antioxidant that protects cell membranes. Vitamin E is also implicated in gene expression and neurological functions. Vitamin E is ingested from diet or supplements. Deficiency of vitamin E can result in ataxia, retinopathy, impaired immune response, peripheral neuropathy, and red blood cell destruction, among other conditions. The UL for vitamin E in healthy adults is 1,000 mg/day.

Tocopherol forms of vitamin E particularly useful in supplementation include α-tocopherol and d-α-tocopherol polyethylene glycol 1000 succinate (TPGS). TPGS is particularly useful in enhancing delivery of lipophilic compounds. In particular TPGS has been shown to increase vitamin D absorption in individuals suffering from chronic childhood cholestasis. Argao et al., *d-Alpha-tocopherol polyethylene glycol-1000 succinate enhances the absorption of vitamin D in chronic cholestatic liver disease of if fancy and childhood*, Ped. Res. 31(2):146-50 (1992). As such, vitamin E in the form of TPGS has particular utility in the formulation of vitamin supplements for individuals suffering from severe malabsorption of fat-soluble vitamins. Further, the enhanced delivery of lipophilic compounds by TPGS is particularly useful in correcting vitamin deficiencies where increasing amounts of fat-soluble vitamins are ineffective and may lead to toxicity. TPGS advantageously enhances delivery of lipophilic compounds, thereby minimizing the risk of toxicity across the spectrum of malabsorption. The compositions disclosed herein comprise vitamin E in the form of TPGS, either alone or in combination with other forms of vitamin E, such as alpha-tocopherol or other forms known in the art.

Vitamin K refers to a group of fat-soluble vitamins that facilitate blood coagulation and binding of calcium in bone and other tissues. Vitamin K includes two natural forms, $K_1$ and $K_2$. Vitamin $K_1$ is also known as phylloquinone, phytomenadione, or phytonadione and is found in abundance in green, leafy vegetables. Vitamin $K_2$ is the main storage form of vitamin K in animals and comprises several subtypes, or menaquinones, characterized by the number of isoprenoid residues in their side chains. Menaquinones are abbreviated MK-n, wherein M indicates menaquinone, K indicates vitamin K, and n represents the number of isoprenoid side chain residues. Vitamin K is also available in synthetic forms, including $K_3$, $K_4$, and $K_5$, although vitamin $K_3$ has shown toxicity. Vitamin K is ingested from diet or supplements and vitamin $K_2$ can be produced in the gut. Deficiency of vitamin K, generally the result of a condition resulting in malabsorption of the vitamin, can result in coagulopathy, osteoporosis, and coronary heart disease. Populations at risk for vitamin K deficiency include those suffering from liver disease, cystic fibrosis, inflammatory bowel disease, or who have had abdominal surgeries. Secondary vitamin K deficiency can occur in those suffering from bulemia, those on strict diets, or individuals taking anticoagulants or certain other drugs. No known toxicity is associated with high doses of vitamin $K_1$ or $K_2$, so no UL has been set.

Vitamin A refers to a group of unsaturated natural organic compounds including retinol, retinyl esters (such as retinyl palmitate), retinal, retinoic acid, and carotenoids such as beta-carotene. Vitamin A is implicated in growth and development, immune system function, and vision. Vitamin A is ingested in supplements or foods such as carrots (beta-carotene), sweet potatoes, squash, and dark leafy greens. Vitamin A deficiency is associated with impaired vision, including night blindness and xerophthalmia. Vitamin A is also important for pregnant and breastfeeding women. The UL for vitamin A in healthy adults is 3,000 mcg/day (10,000 RJ). Hypervitaminosis A can cause anorexia, dry itchy skin, alopecia, bone pain, increased intracranial pressure, and hepatosplenomegaly. In certain embodiments of the present compositions, the inclusion of beta-carotene as a form of vitamin A allows for a reservoir of vitamin A as may be needed by the subject, without causing hypervitaminosis A, which can be toxic. Moreover, a combination of vitamin A from different sources, including a combination of retinyl esters (such as retinyl palmitate) and beta-carotene together, imparts advantageous stability to the scalable vitamin compositions disclosed herein.

In malabsorbers, supplementation requirements of vitamins D, E, K, and A can be much higher that the IOM-defined upper intake levels. Further, the disease conditions associated with malabsorption may increase the requirement for these nutrients. For example, recommendations for vitamin D in adult cystic fibrosis patients with moderate malabsorption begin at 800-2,000 IU/day and can go up to 10,000 IU/day. In the case of severe cholestatic liver disease, such as biliary atresia, there are no defined upper boundaries for these fat-soluble vitamins, with doses sometimes as high as 25 IU/kg/day of vitamin E in infants.

In one embodiment, a scalable vitamin composition unit dosage is provided, wherein the unit dosage consists essentially of vitamin D, vitamin E, vitamin K, and vitamin A. In a particular embodiment, the scalable unit dosage is substantially free of additional vitamins. In another particular embodiment, the unit dosage is scalable based on weight, age, sex, and condition of a subject, without inducing adverse toxic effects.

Scalable, as used herein, refers to a property of a unit dosage, wherein the unit dosage can be significantly increased (e.g., multiplied by a scaling factor) to meet the requirements of a person suffering from vitamin malabsorption, based on age, body weight, physiological status, and disease condition, without causing undesired side effects such as toxicity. Many common multivitamin supplements contain minerals such as selenium, which can be toxic if the unit dose is increased significantly to meet the requirements of, for example, malabsorbing children for vitamins D, E, K, and A. As such, typical common multivitamins are not scalable, since significantly increasing the unit dosage to meet the requirements of a malabsorber would introduce toxicity from other vitamins. In contrast, the presently disclosed embodiments are scalable, such that increasing the unit dosage meets the requirements of such a malabsorber, without causing toxicity.

The ratios and sources of the fat-soluble vitamins D, E, K, and A in the presently disclosed embodiments are selected to provide a vitamin composition that is uniquely scalable. The weight ratio of active vitamins D:E:K:A, together with the particular sources of the vitamins selected, provide vitamin compositions that can be scaled up to treat malabsorption, while minimizing toxicity. TPGS is particularly useful in enhancing delivery of fat-soluble vitamins, while the combination of retinyl palmitate and beta-carotene provide enhanced stability for vitamin A. When vitamin E is provided as TPGS or a mixture of TPGS and another form of vitamin E and vitamin A is provided as a combination of retinyl palmitate and beta-carotene, respectively, and the D:E:K:A weight ratio is within the selected range, a uniquely scalable composition is provided, wherein the unit dosage can be scaled up to treat varying degrees of malabsorption, while minimizing toxicity to the subject.

In one embodiment, the vitamin composition unit dosage provided herein is a liquid unit dosage that is scalable while maintaining a weight ratio of active vitamins D:E:K:A that is about 0.75-1.25:750-1250:30-50:9-15. In a more specific embodiment, the weight ratio for a liquid composition is about 0.9-1.1:900-1100:35-45:10-14. In a very specific embodiment, the weight ratio for a liquid composition is about 1:1007:40:12. In another specific embodiment, the weight ratio for a liquid composition is about 1:1007:40:12, wherein each value in the ratio may vary by up to 25%, up to 10%, up to 5%, or up to 1%.

In another embodiment, the vitamin composition unit dosage provided herein is a solid unit dosage, such as a capsule or a tablet, which is scalable while maintaining a weight ratio of active vitamins D:E:K:A that is about 0.75-1.25:1500-2500:15-25:9-15. In a more specific embodiment, the weight ratio for a solid composition is about 0.9-1.1:1800-2200:17-23:10-14. In a very specific embodiment, the weight ratio for a solid composition is about 1:2013:20:12. In another specific embodiment, the weight ratio for a solid composition is about 1:2013:20:12, wherein each value in the ratio may vary by up to 25%, up to 10%, up to 5%, or up to 1%.

Unit dosages are then scaled up by multiplying the unit dosage (e.g., 0.5 ml or 1 ml of a liquid formulation, or a single solid dosage form) by a scaling factor (e.g., a whole or fractional number) in order to deliver vitamins D, E, K, and A in beneficial proportions, while tailoring dose to meet the needs of the individual.

The skilled artisan may take into consideration the age, sex, weight, medical condition, and severity of malabsorption of a subject when determining the appropriate scaled dose of the instant unit dosage. For example, the skilled artisan will consider medical conditions in an individual which cause malabsorption of fat-soluble vitamins. The skilled artisan will consider the severity of any such condition in determining the proper scaled dose to meet individual needs.

In one embodiment, vitamin D is in a form selected from the group consisting of cholecalciferol, ergocalciferol, and combinations thereof. In a specific embodiment, vitamin D is in the form of cholecalciferol. A unit dosage disclosed herein may comprise from about 500 to about 4000 IU vitamin D, including cholecalciferol or ergocalciferol. In a liquid composition, a unit dosage disclosed herein may comprise from about 500 to about 2500 IU/ml vitamin D. In a specific embodiment, a liquid composition comprises about 2000 IU/ml cholecalciferol. In a solid or capsule composition, a unit dosage disclosed herein may comprise from about 1000 to about 4000 IU vitamin D. In a specific embodiment, a solid or capsule composition comprises about 2000 IU vitamin D.

In one embodiment, vitamin E is in a form selected from α-tocopherol and d-α tocopheryl polyethylene glycol 1000 succinate (TPGS). In a very specific embodiment, vitamin E is in the form of TPGS or a combination of TPGS and another form of vitamin E. A unit dosage disclosed herein may comprise from about 18 to about 300 IU vitamin E in the form of TPGS. In a liquid composition, a unit dosage disclosed herein may comprise from about 18 to about 150 IU/ml vitamin E in the form of TPGS. In a specific embodiment, a liquid composition comprises about 75 IU/ml vitamin E in the form of TPGS. In a solid or capsule composition, a unit dosage may comprise from about 75 to about 300 IU vitamin E. In a specific embodiment, a solid or capsule composition comprises about 150 IU vitamin E.

In one embodiment, vitamin K is in a form selected from the group consisting of phytonadione, menaquinone, and combinations thereof. In a specific embodiment, vitamin K is in the form of phytonadione. A unit dosage disclosed herein may comprise from about 500 to about 4000 micrograms (mcg) vitamin K in the form of phytonadione and/or menaquinone. In a liquid composition, a unit dosage disclosed herein may comprise from about 500 to about 2500 mcg/ml vitamin K in the form of phytonadione and/or menaquinone. In a specific embodiment, a liquid composition comprises about 2000 mcg/ml vitamin K in the form of phytonadione and/or menaquinone. In a solid or capsule composition, a unit dosage disclosed herein may comprise from about 500 to about 4000 mcg vitamin K. In a specific embodiment, a solid or capsule composition comprises about 1000 mcg vitamin K.

In one embodiment, vitamin A is in a form selected from the group consisting of retinol, retinyl esters, retinal, retinoic acid, carotenoids, and combinations thereof. In a specific embodiment, vitamin A is in a form selected from the group consisting of retinyl palmitate, beta-carotene, and combinations thereof. A unit dosage disclosed herein may comprise from about 500 to about 4000 IU vitamin A. In a liquid composition, a unit dosage disclosed herein may comprise from about 500 to about 2500 IU/ml vitamin A. In a specific embodiment, a unit dosage comprises about 2000 IU/ml vitamin A. In a solid or capsule composition, a unit dosage may comprise from about 1000 to about 4000 IU vitamin A. In a specific embodiment, a solid or capsule composition comprises about 2000 IU vitamin A.

In certain embodiments, any of the unit dosages described herein are provided in the form of a liquid, a softgel, a tablet, a chewable tablet, a bar, a sublingual dosage form, or a gummy dosage form. The skilled artisan will appreciate that the suitable amounts of vitamins D, E, K, and A will vary, depending on the form of the unit dosage.

In a specific embodiment, a scalable vitamin composition unit dosage is provided in liquid form, the unit dosage consisting essentially of: about 2000 IU/ml vitamin D in the form of cholecalciferol; about 75 IU/ml vitamin E in the form of TPGS; about 2000 mcg/ml vitamin K in the form of phytonadione; and about 2000 IU/ml vitamin A in the form of a combination of retinyl palmitate and beta-carotene.

In another specific embodiment, a scalable vitamin composition unit dosage is provided in solid or capsule form, the unit dosage consisting essentially of: about 2000 IU vitamin D in the form of cholecalciferol; about 150 IU vitamin E in the form of TPGS or a combination of TPGS and another form of vitamin E; about 1000 mcg vitamin K in the form of phytonadione; and about 2000 IU vitamin A in the form of a combination of retinyl palmitate and beta-carotene.

In another embodiment, any of the unit dosages described herein further comprise an emulsifier. In specific embodiments, the emulsifier is selected from the group consisting of monoglycerides, diglycerides, triglycerides, lecithin, polyethylene glycol, acacia gum, fatty alcohols, monostearate, polysorbates, pectin, cellulose, cellulose derivatives, ceteareth, and combinations thereof, although the skilled artisan will appreciate that many emulsifiers known in the art may be suitable for use.

Also provided herein is a method of treating a fat-soluble vitamin deficiency in a subject in need thereof, the method comprising administering to the subject an effective amount of any of the unit dosages disclosed herein.

In one embodiment, a method of treating a fat-soluble vitamin deficiency in a subject in need thereof is provided, the method comprising:

a) providing a scalable vitamin composition unit dosage consisting essentially of: from about 500 to about 4000 IU vitamin D in the form of cholecalciferol; from about 18 to about 300 IU vitamin E in the form of alpha-tocopherol from TPGS or a combination of TPGS and another form of vitamin E; from about 500 to about 4000 mcg vitamin K in the form of phytonadione; and from about 500 to about 4000 IU vitamin A in a form selected from a combination of retinyl palmitate and beta-carotene;

b) determining the levels of vitamins D, E, K, and A needed to treat the fat-soluble vitamin deficiency;

c) scaling up the unit dosage provided in step (a) by multiplying the unit dosage by a scaling factor in order to provide the levels determined in step (b); and d) administering the scaled dosage of step (c), wherein the fat-soluble vitamin deficiency is treated in the subject without inducing toxic effects.

EXAMPLES

The following examples are given by way of illustration and are in no way intended to limit the scope of the present invention.

Example 1

Figure 3:
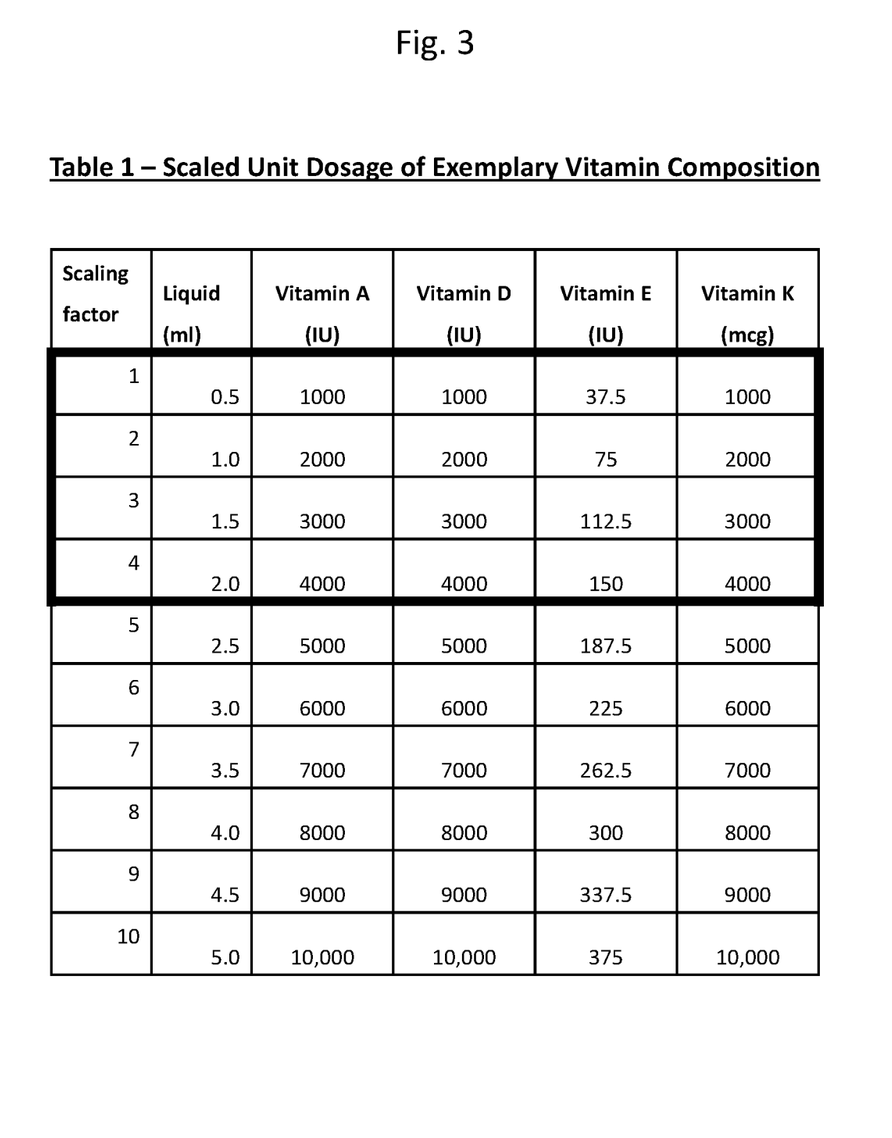
FIG. 3 is a table showing the dosage amounts of vitamins D, E, K, and A delivered when the unit dosage is multiplied by a scaling factor.

The presently disclosed vitamin composition unit dosage is scalable to allow for appropriate dosing of the fat-soluble vitamins D, E, K, and A based on the degree of malabsorption due to an individual's particular disease state. Referring to FIG. 3, Table 1 shows the dosage amounts of vitamins D, E, K, and A delivered when the unit dosage is multiplied by a scaling factor in order to deliver increased amounts to the individual in need thereof.

As shown in Table 1, the unit dosage per 0.5 ml is scalable to up to four or more times the base dose for healthy children to adults (area of Table 1 enclosed in bold border). This permits more precise dosing of the fat-soluble vitamins depending on the particular condition of the person to be treated. Further, patients with malabsorption may require multiple times the UL dose for healthy adults. Accordingly, the instant unit dosage composition may be scaled up by a factor higher than four in order to treat individuals impacted by severe malabsorption. The skilled artisan will understand that the scaling factors 2-10 are given by way of example only, and that it is within the purview of the skilled artisan to determine the appropriate factor by which to scale the unit dosage, including fractional factors and factors exceeding 10, should the case warrant. Because the instantly disclosed formulations omit vitamins other than D, E, K, and A, the skilled artisan can scale up the vitamin dose without introducing toxicity due to other vitamins/minerals.

Figure 4:
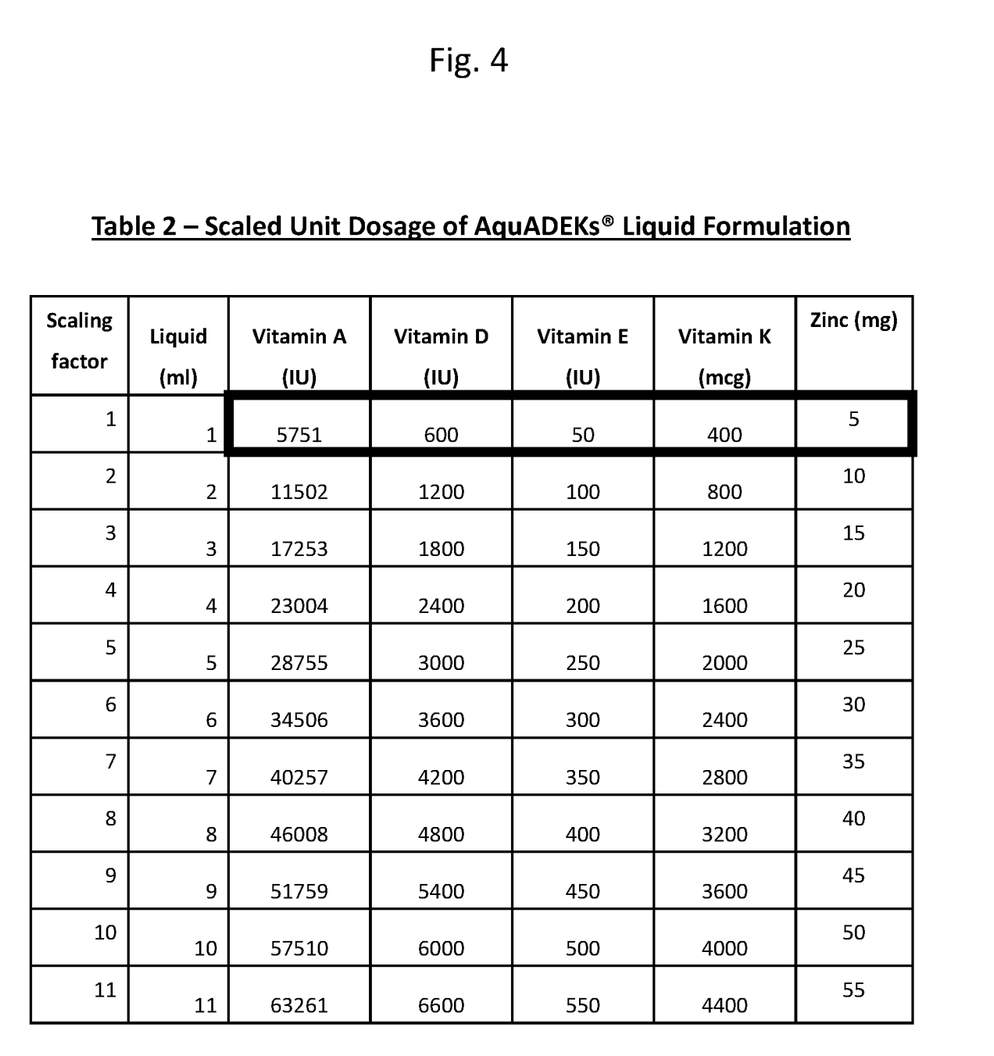
FIG. 4 is a table showing the scaled dosage amounts of certain vitamins included in AquADEKS® liquid vitamin supplement formulation.

Other available vitamin compositions contain levels of vitamins D, E, K, and A that are insufficient, at the recommended dosages, to meet the requirements of patients with severe malabsorption. However, higher dosages of those compositions would lead to toxicity of other vitamins included in the composition (for example, zinc, iron, or even vitamin A in some instances). Referring to FIG. 4, Table 2 shows the dosage amounts of certain vitamins included in AquADEKS® liquid vitamin supplement formulation (Aptalis). The area of Table 2 enclosed in bold border shows levels below the UL for zinc for a child 1-3 years of age.

As shown in Table 2, if the AquADEKs® formulation were scaled up to accommodate the daily vitamin D needs of a severe malabsorber (e.g., 4000 IU vitamin D/day), one would have to administer over 6 ml AquADEKs®, and in so doing, would deliver a level of zinc that is above the UL of zinc for children 1-3 years of age (7 mg/day).

Figure 5:
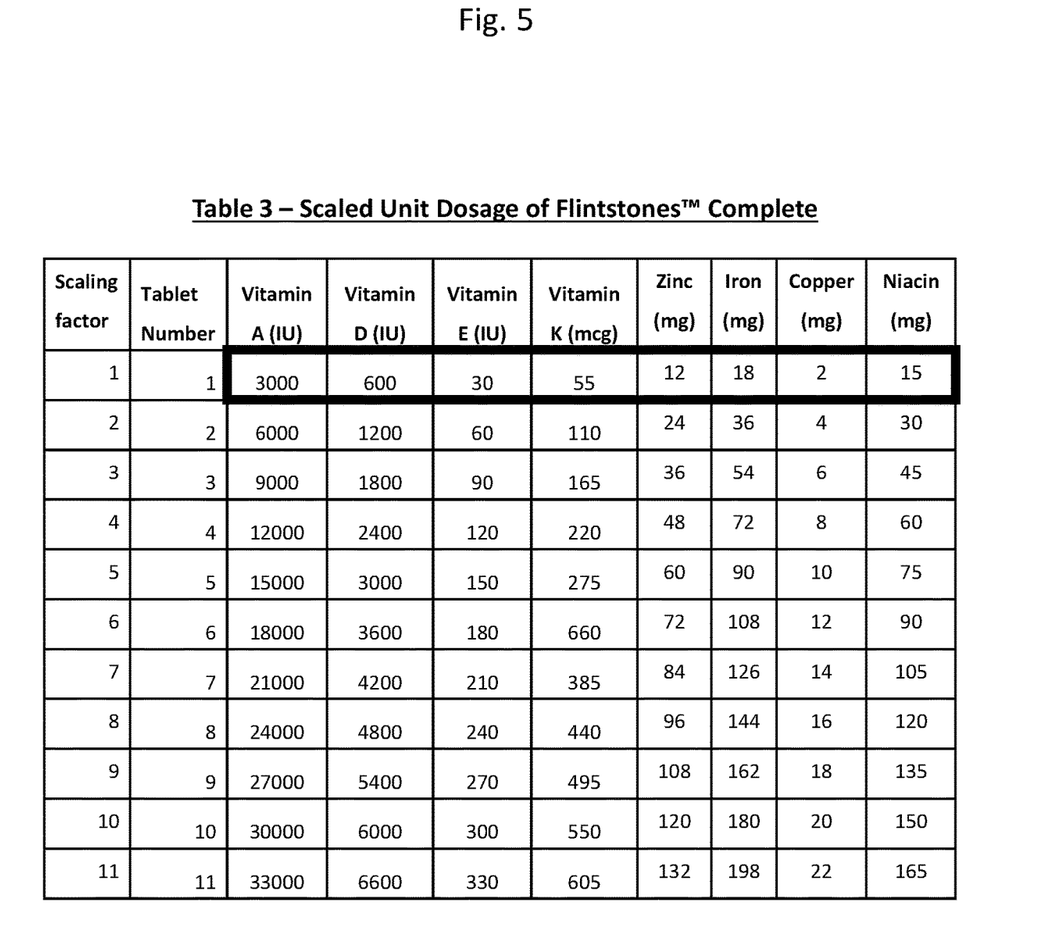
FIG. 5 is a table showing the scaled dosage amounts of certain vitamins included in Flintstones™ Complete vitamin supplement formulation.

Referring to FIG. 5, Table 3 shows the dosage amounts of certain vitamins included in Flintstones™ Complete vitamin supplement formulation (Bayer HealthCare). The area of Table 3 enclosed in bold border shows levels below the UL for zinc in a child 4-8 years of age.

As shown in Table 3, if the Flintstones™ Complete formulation were scaled up to accommodate the daily vitamin D needs of a severe malabsorber (e.g., 4000 IU vitamin D/day), one would have to administer 7 tablets, and in so doing, would deliver levels of zinc, iron, copper, and niacin that are above the respective ULs for a child 4-8 years of age (zinc, 12 mg/day; iron, 40 mg/day; copper, 3 mg/day; niacin, 15 mg/day).

Figure 6:
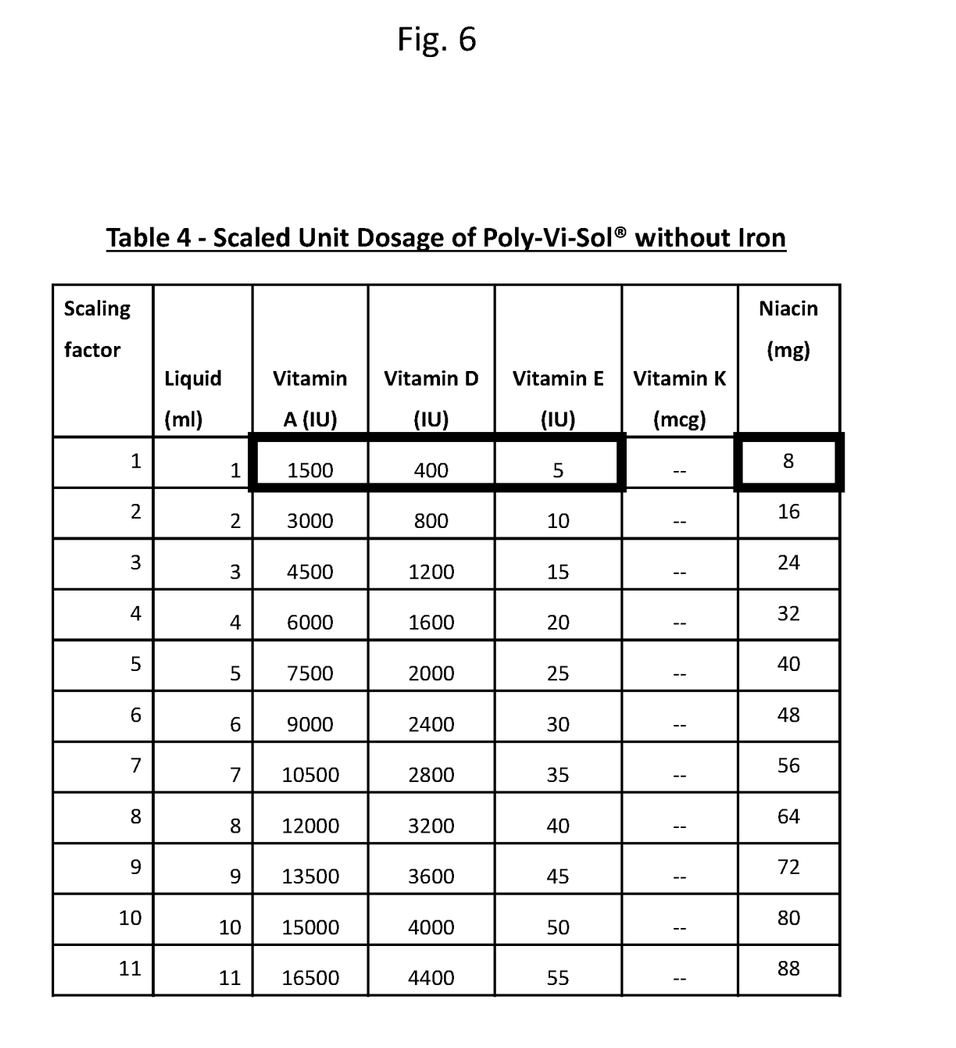
FIG. 6 is a table showing the scaled dosage amounts of certain vitamins included in Poly-Vi-Sol® vitamin supplement formulation.

Referring to FIG. 6, Table 4 shows the dosage amounts of certain vitamins included in Poly-Vi-Sol® vitamin supplement formulation (Enfamil US). The area of Table 4 enclosed in bold border shows levels below the UL for a child 1-3 years of age.

As shown in Table 4, if the Poly-Vi-Sol® formulation were scaled up to accommodate the daily vitamin D needs of a severe malabsorber (e.g., 4000 IU vitamin D/day), one would have to administer 10 ml Poly-Vi-Sol®, and in so doing, would deliver a level of niacin that is above the UL for children 1-3 years of age (niacin, 10 mg/day). Further, Poly-Vi-Sol® fails to include vitamin K, a fat-soluble vitamin often deficient in malabsorbers.

Together, Tables 2-4 illustrate the difficulties of scaling up current multivitamins to meet the needs of malabsorbers, while avoiding toxicity. As shown in table 1, the formulas of the instant invention can be safely scaled up to meet the needs of malabsorbers, without introducing toxic effects.

Example 2

Table 5 below shows the weight (mg) per volume liquid suspension (ml) for an exemplary scalable unit dosage of the present invention, wherein weight ratios of vitamins D, E, K, and A are maintained in order to provide benefits to malabsorbers while avoiding toxicity.

TABLE 5

Scaled Unit Dosage of Exemplary Vitamin Composition

| Scaling Factor | Liquid (ml) | Vitamin D (mg) as cholecalciferol | Vitamin E (mg) as alpha-tocopherol TPGS | Vitamin K (mg) as phytonadione | Vitamin A (mg) as retinol from retinyl palmitate |
|---|---|---|---|---|---|
| 1 | 0.5 | 0.025 | 25.2 | 1 | 0.3 |
| 2 | 1.0 | 0.05 | 50.3 | 2 | 0.6 |
| 3 | 1.5 | 0.075 | 75.5 | 3 | 0.9 |
| 4 | 2.0 | 0.1 | 100.7 | 4 | 1.2 |
| 5 | 2.5 | 0.125 | 125.8 | 5 | 1.5 |
| 6 | 3.0 | 0.15 | 151.0 | 6 | 1.8 |

In the exemplary composition of Table 5, weight ratio (mg) of vitamins D:E:K:A is about 1:1007:40:12 (wherein the weight ratio is calculated based on the weight in mg of each active vitamin, and not the weight of the raw material source of the active vitamin). The unit dosage is scaled up by multiplying the unit dosage (e.g., 0.5 ml of a liquid formulation) by a scaling factor (e.g., a whole or fractional number) in order to deliver vitamins D, E, K, and A in beneficial proportions, while tailoring dose to meet the needs of the individual suffering from malabsorption.

Example 3

Table 6 provides exemplary scalable unit doses for capsule and liquid formulations.

TABLE 6

Unit Doses for Capsule and Liquid Formulations

| | Dose | Vitamin A retinyl palmitate/ beta-carotene combination | Vitamin D cholecalciferol | Vitamin E alpha-tocopherol TPGS | Vitamin K phytonadione |
|---|---|---|---|---|---|
| DEKAs Essential Capsule | 1 capsule | 2000 IU | 2000 IU | 150 IU (TPGS + alpha tocopherol) | 1000 mcg |
| DEKAs Essential Liquid | 0.5 ml | 1000 IU | 1000 IU | 37.5 IU | 1000 mcg |
| DEKAs Essential Liquid | 1 ml | 2000 IU | 2000 IU | 75 IU | 2000 mcg |

The invention claimed is:

1. A scalable oral vitamin composition unit dosage adapted to treat a fat-soluble vitamin deficiency in a subject suffering from chronic malabsorption of fat-soluble vitamins, the unit dosage consisting essentially of:
   from about 500 to about 4000 IU vitamin D in the form of cholecalciferol;
   from about 18 to about 300 IU vitamin E in the form of d-alpha tocopheryl polyethylene glycol 1000 succinate (TPGS) or a combination of TPGS and another form of vitamin E;
   from about 500 to about 4000 mcg vitamin K in the form of phytonadione; and
   from about 500 to about 4000 IU vitamin A in the form of a combination of retinyl palmitate and beta-carotene;
   wherein the unit dosage is substantially free of additional vitamins, and wherein the unit dosage is scalable to satisfy fat-soluble vitamin supplementation requirements of the subject suffering from chronic malabsorption without inducing adverse toxic effects.

2. The unit dosage of claim 1, wherein the unit dosage is in the form of a liquid, a softgel, a tablet, a capsule, a chewable tablet, a bar, a sublingual dosage form, or a gummy dosage form.

3. The unit dosage of claim 1, further comprising an emulsifier.

4. The unit dosage of claim 3, wherein the emulsifier is selected from the group consisting of monoglycerides, diglycerides, triglycerides, lecithin, polyethylene glycol, acacia gum, fatty alcohols, monostearate, polysorbates, pectin, cellulose, cellulose derivatives, ceteareth, and combinations thereof.

5. A method of treating a fat-soluble vitamin deficiency in a subject in need thereof, the method comprising administering to the subject an effective amount of the unit dosage according to claim 1.

6. The unit dosage of claim 1, wherein the unit dosage is a liquid and consists essentially of:
   about 2000 IU/ml cholecalciferol;
   about 75 IU/ml alpha-tocopherol from TPGS;
   about 2000 mcg/ml phytonadione; and
   about 2000 IU/ml of a combination of retinyl palmitate and beta-carotene.

7. The unit dosage of claim 6, wherein the weight ratio of vitamins D:E:K:A is about 1:1007:40:12, wherein each value in the weight ratio may vary independently by ±10%.

8. The unit dosage of claim 1, wherein the unit dosage is a capsule and consists essentially of:
   about 2000 IU cholecalciferol;
   about 150 IU alpha-tocopherol from TPGS or a combination of TPGS and another form of vitamin E;
   about 1000 mcg phytonadione; and
   about 2000 IU of a combination of retinyl palmitate and beta-carotene.

9. The unit dosage of claim 8, wherein the weight ratio of vitamins D:E:K:A is about 1:2013:20:12, wherein each value in the weight ratio may vary independently by ±10%.

10. A method of treating a fat-soluble vitamin deficiency in a subject suffering from chronic malabsorption of fat-soluble vitamins, the method comprising:
    a) providing a scalable oral vitamin composition unit dosage consisting essentially of: from about 500 to about 4000 IU vitamin D in the form of cholecalciferol; from about 18 to about 300 IU vitamin E in the form of alpha-tocopherol from TPGS or a combination of TPGS and another form of vitamin E; from about 500 to about 4000 mcg vitamin K in the form of phytonadione; and from about 500 to about 4000 IU vitamin A in the form of a combination of retinol from retinyl palmitate and beta-carotene;
    b) determining the levels of vitamins D, E, K, and A needed to treat the fat-soluble vitamin deficiency;
    c) scaling up the unit dosage provided in step (a) by multiplying the unit dosage by a scaling factor in order to provide the levels determined in step (b); and
    d) administering the scaled dosage of step (c),
    wherein the fat-soluble vitamin deficiency is treated in the subject without inducing toxic effects.

11. The method of claim 10, wherein the scalable vitamin composition unit dosage is a liquid consisting essentially of: from about 500 to about 2500 IU/ml cholecalciferol, from about 18 to about 150 IU/ml alpha-tocopherol from TPGS; from about 500 to about 2500 mcg/ml phytonadione; and from about 500 to about 2500 IU/ml of a combination of retinyl palmitate and beta-carotene.

12. The method of claim 10, wherein the scalable vitamin composition unit dosage is a capsule consisting essentially of: from about 1000 to about 4000 IU cholecalciferol, from about 75 to about 300 IU alpha-tocopherol from TPGS or a combination of TPGS and another form of vitamin E; from about 500 to about 4000 mcg phytonadione; and from about 500 to about 4000 IU of a combination of retinyl palmitate and beta-carotene.

13. The unit dosage of claim 1, wherein the unit dosage is a liquid and a weight ratio of vitamins D:E:K:A is about 0.75-1.25:750-1250:30-50:9-15.

14. The unit dosage of claim 1, wherein the unit dosage is a solid and a weight ratio of vitamins D:E:K:A is about 0.75-1.25:1500-2500:15-25:9-15.

* * * * *

UNITED STATES PATENT AND TRADEMARK OFFICE
CERTIFICATE OF CORRECTION

PATENT NO. : 10,688,107 B2
APPLICATION NO. : 15/558622
DATED : June 23, 2020
INVENTOR(S) : Konstantinos Andreas Papas

Page 1 of 1

It is certified that error appears in the above-identified patent and that said Letters Patent is hereby corrected as shown below:

In the Specification

In Column 5, Line(s) 20 & 21, delete "(10,000 RJ)" and insert --(10,000 IU)--, therefor.

Signed and Sealed this
Eleventh Day of August, 2020

Andrei Iancu
*Director of the United States Patent and Trademark Office*